(12) United States Patent
Barrett (10) Patent No.: US 8,613,773 B2
(45) Date of Patent: Dec. 24, 2013

(54) DISC NUCLEUS REPLACEMENT

(75) Inventor: Patrick Barrett, Jackson, MS (US)

(73) Assignee: Spinal U.S.A., Pearl, MS (US)

( * ) Notice: Subject to any disclaimer, the term of this patent is extended or adjusted under 35 U.S.C. 154(b) by 632 days.

(21) Appl. No.: 12/329,125

(22) Filed: Dec. 5, 2008

(65) Prior Publication Data

US 2009/0210063 A1   Aug. 20, 2009

Related U.S. Application Data

(60) Provisional application No. 60/992,528, filed on Dec. 5, 2007.

(51) Int. Cl.
*A61F 2/44* (2006.01)
(52) U.S. Cl.
USPC ........................................... 623/17.16

(58) Field of Classification Search
USPC ............................................. 623/17.11–17.16
See application file for complete search history.

(56) References Cited

U.S. PATENT DOCUMENTS

| | | | |
|---|---|---|---|
| 7,267,690 B2 * | 9/2007 | Felt | 623/17.11 |
| 2002/0029084 A1 * | 3/2002 | Paul et al. | 623/23.63 |
| 2006/0106462 A1 * | 5/2006 | Tsou | 623/17.16 |
| 2006/0247778 A1 * | 11/2006 | Ferree et al. | 623/17.14 |
| 2007/0260318 A1 * | 11/2007 | Lawson | 623/17.16 |
| 2008/0208343 A1 * | 8/2008 | Felt | 623/17.16 |

\* cited by examiner

*Primary Examiner* — Ellen C Hammond
(74) *Attorney, Agent, or Firm* — Cermak Nakajima LLP; Adam J. Cermak (57) ABSTRACT

An artificial disc nucleus replacement includes two mating halves which are inserted into the patient from opposite lateral sides of the patient's back, and joined together with screws.

8 Claims, 8 Drawing Sheets

DISC NUCLEUS REPLACEMENT

This application claims priority under 35 U.S.C. §119 to U.S. provisional application No. 60/992,528, filed 5 Dec. 2007, the entirety of which is incorporated by reference herein.

BACKGROUND

1. Field of Endeavor

The present invention relates to devices, systems, and processes useful in disc nucleus replacement.

2. Brief Description of the Related Art

A disc nucleus replacement device is designed to replace only the inner portion of the disc (the nucleus). A variety of disc nucleus replacement technologies have been investigated in the laboratory, and some have been implanted in countries outside the US. Various materials are utilized in these implants, including metals and ceramics, injectable fluids, hydrogels, inflatables, and elastic coils.

Early attempts at disc replacement were all nuclear replacements, based on the need to prevent disc space collapse following discectomy. David Cleveland published the first study in 1955, when he injected methyl-acrylic into the disc space at the time of discectomy in 14 patients. James Gardner reported to have "replaced hundreds of damaged lumbar discs with 8×22 mm Lucite pegs, yielding excellent results." Hamby reported reproduction of Cleveland's work in another 14 patients, reported in 1957 at the American Association of Neurological Surgeons meeting. In 1959, Harmon implanted Vitallium Spheres, inserted through an anterior retroperitonael approach, but never reported his results. Nicholson injected silicon rubber inserts into cadaveric discs in 1962, but never proceeded to clinical trials since the implants did poorly in mechanical testing. In 1964, Fernstrom published results of replacing lumbar discs with a metal ball bearing, under local anesthesia. At 30 months, he stated that his results were better than discectomy alone, and comparable to fusion. Similarly, Reitz and Joubert implanted 19 steel balls into 12 patients, and at 8-month follow-up concluded that results were superior to fusion.

Presently, there are several disc nucleus replacement technologies in various stages of development. The following outlines a few of the better-known technologies.

Prosthetic Disc Nucleus (PDN): The Raymedica PDN ("Prosthetic Disc Nucleus") has been implanted outside the US in several experimental series and just recently the PDN-SOLO device has been implanted in the US as part of a non-randomized, prospective clinical trial. The PDN is composed of a hydrogel core in a flexible, inelastic, woven polyethylene jacket. The hydrogel undergoes a cyclic swelling and shrinking, depending on load.

The Newcleus: The Newcleus utilizes an elongated elastic memory-coiling spiral made of polycarbonate urethane. It is inserted through a posterolateral annulotomy after discectomy, and then spirals around within the annulus to fill the nuclear cavity. This device has undergone laboratory and animal investigation, and has been implanted in a small number of patients in Europe.

Aquarelle Hydrogel Nucleus: The Aquarelle Hydrogel Nucleus (by Stryker Howmedica Osteonic) is composed of a polyvinyl alcohol material. Biomechanical testing indicates that it has a performance similar to the intact nucleus. Some implants have been implanted in humans in Europe, and Baboon studies have been initiated in the US.

Other implants include:

Interpore Cross International has developed a one-piece convex surfaced ceramic or metal implant that anchors to the inferior vertebral body as a hemiarthroplasty. It has been implanted in 2 patients, and animal studies in the US have been initiated.

Disc Dynamics has tested a balloon-like implant made of polyurethane, which is implanted through a cannula (tube), and animal studies have been initiated.

Cryolife has tested the Biodisc, a protein hydrogel device that is injected into the nuclear cavity in a fluid form, but it rapidly hardens.

Disc Augmentation Technologies initiated mechanical studies on a thermopolymer that also hardens inside the disc after being injected as a fluid.

Replication Medical's Aquacryl is a hydrogel undergoing mechanical testing.

Ultimately, the results of clinical trials will determine the efficacy of any of these nucleus replacements. Potential problems include migration of the device, end-plate changes, and vitality of the annulus following an annulotomy for insertion.

There remains a significant need for the development of a disc replacement that addresses some or all of the deficiencies in these prior devices.

SUMMARY

According to a first aspect of the invention, a disc nucleus replacement comprises a first portion having a top, a bottom, a generally semi-circular lateral outer surface extending between the top and the bottom, a flat outer lateral surface extending between the top and the bottom, and at least one bore extending through the first portion from the semi-circular lateral outer surface and the flat outer surface, a second portion having a top, a bottom, a generally semi-circular lateral outer surface extending between the top and the bottom, a flat outer lateral surface extending between the top and the bottom, and at least one bore extending through the second portion from the flat outer surface towards the semi-circular lateral outer surface, and wherein the at least one bore of the first portion, the at least one bore of the second portion, the semi-circular lateral outer surface of the first portion, and the semi-circular lateral outer surface of the second portion are mutually configured and arranged so that when the first and second portions are oriented with the flat surfaces abutting and the semi-circular lateral outer surfaces forming a generally circular form, the at least one bore of the first portion aligns with the at least one bore of the second portion to permit a single screw to be positioned therein.

According to another aspect of the present invention, a method of implanting a disc nucleus replacement into a disc of a patient, the disc nucleus replacement having two mating portions, the nucleus of the patient's disc having previously been removed, comprises forming two lateral incisions in the disc, pushing one portion of the disc nucleus replacement through one of the lateral incisions and into place in the center of the patient's disc, and pushing a second mating portion of the disc nucleus replacement through the same or the other lateral incision and adjacent to and into alignment with the first portion of the disc nucleus replacement.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Referring to the drawing figures, like reference numerals designate identical or corresponding elements throughout the several figures.

The purpose of a disc replacement is to replace only the inner portion of the disc (the nucleus). The nucleus portion of the disc impinges on a nerve root and causes the disc to collapse, which causes back pain for the patient. In the past, the usual procedure was to take out the disc and fuse the vertebral bodies together. A disc replacement embodying principles of the present invention is used to replace only the inner portion of the disc (the nucleus) through two minimum incisions, which will speed the patient's recovery time by months and the patient will be able to leave the hospital the same day and back to work or play within days.

A disc nucleus replacement embodying principles of the present invention preferably replaces only the inner portion of the disc (the nucleus). With reference to the drawing figures, in which two exemplary embodiments are illustrated, the disc replacement is a generally round device made from titanium, peek, ceramic material, or any other material which exhibits sufficient material properties to function as a spinal implant. The disc replacement is formed in two parts, which are inserted through a minimum incision on both sides of, e.g., the lower back of the human patient. The first portion of the device is inserted on one side of the lower back and then the second device is inserted from the other side and then two screws are inserted through the minimum incision into the devices; the screws pull the two halves together to form a disc nucleus. The screws are made from titanium, peek, or ceramic material, or other material as discussed above. Optionally, the two pieces of the disc replacement are joined together with a sliding dovetail joint, which are assembled by sliding the tail on one of the pieces into the socket, formed in the other piece, of the dovetail. As is common for dovetail joints, the tail and/or the socket are slightly tapered from one lateral side of the piece to the other, making it slightly tighter towards the end of the joint when the pieces are nearly completely assembled, so that the two pieces can be slid together easily but the joint becomes tighter as the finished position is reached. Further optionally, the center of the tail and/or socket is slightly larger than the lateral ends, that is, one or both components of the dovetail have a double taper, so that the two pieces can be slide together from either end and the joint tightens up as the come close to their final assembled configuration.

In further general terms, the exemplary disc nucleus replacements described herein, and each of their respective pieces, are advantageously, yet not necessarily, symmetrical in two orthogonal planes: a vertical plane through the geometric center of the device, splitting the disc replacement into mirrored left and right lateral halves; and a horizontal plane through the geometric center of the device, splitting the disc replacement into mirrored top and bottom halves. Thus, the following descriptions are made only with reference to one quadrant of each of the discs or pieces thereof, so as to not obfuscate aspects of the present invention, it being therefore understood that the left-right and top-bottom symmetries of embodiments of the invention determine the structures of the other three quadrants. The present invention is not so limited, however, and other embodiments include asymmetrical disc nucleus replacements, in particular embodiments in which the top and bottom surfaces are differently configured in order to better match the portions of the disc left after removal of a damaged or diseased disc nucleus which lie above and below the disc nucleus replacement.

Figure 1:
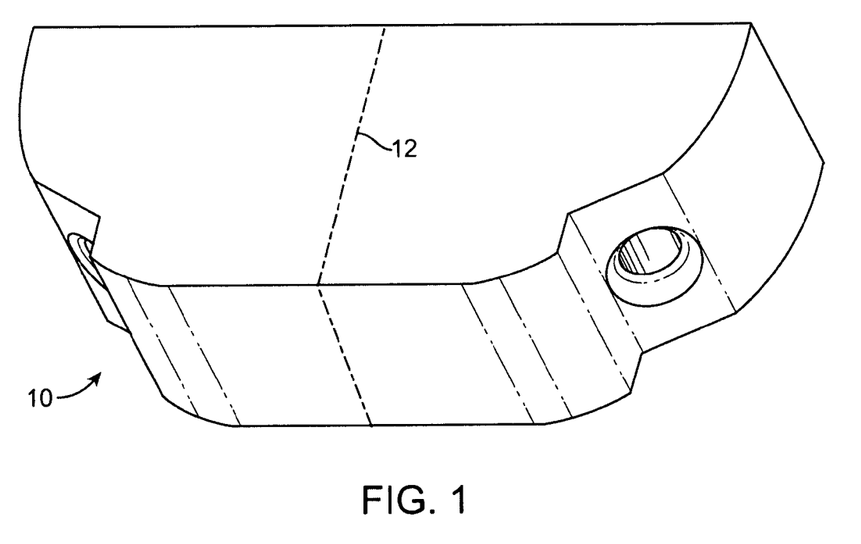
FIG. 1 illustrates a perspective view of a first embodiment of a first half of a two-piece disc replacement embodying principles of the present invention.

Turning now to the drawing figures, FIG. 1 illustrates a first exemplary embodiment of a first portion 10 of a disc nucleus replacement embodying principles of the present invention. The first portion 10, as discussed above, is advantageously, yet not necessarily, symmetrical about a plane 12 bisecting the first portion 10 through the geometric center of the first portion. More features of the first embodiment of the first portion will be described elsewhere herein.

Figure 2:
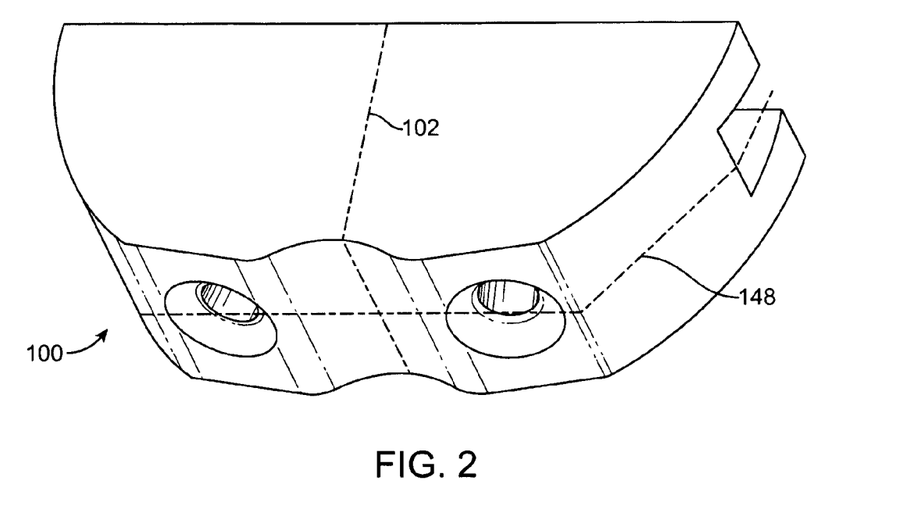
FIG. 2 illustrates a perspective view of a second embodiment of a first half of a two-piece disc replacement embodying principles of the present invention.
Figure 3:
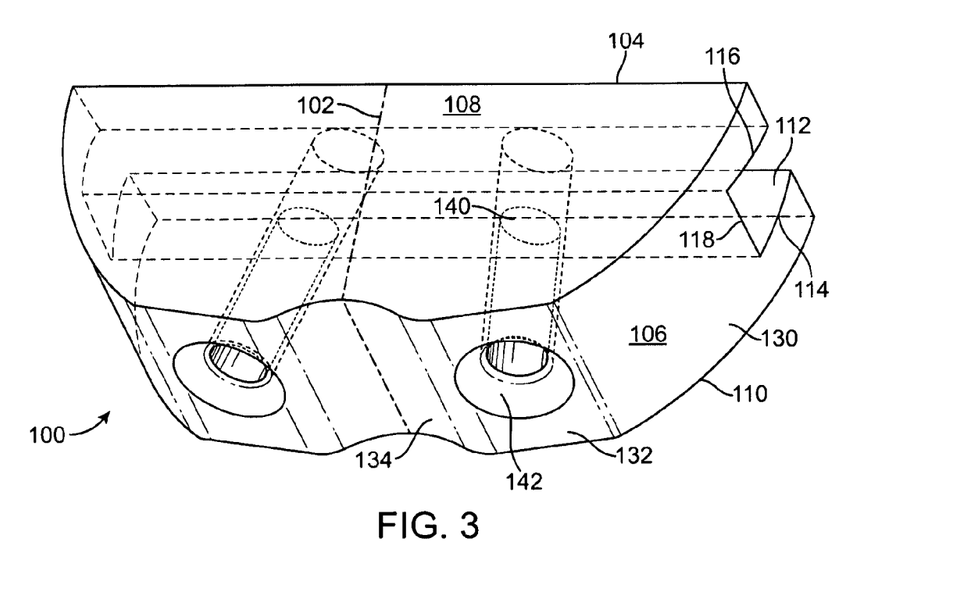
FIG. 3 illustrates a wire-frame perspective view of the first half illustrated in FIG. 2.

FIGS. 2 and 3 illustrate a second embodiment of a first portion 100 of a disc nucleus replacement embodying principles of the present invention. Like the first embodiment illustrated in FIG. 1, and as discussed above, the first portion 100 is advantageously symmetrical about planes 102, 148. The first portion 100 includes a flat interior surface 104, interior because when assembled with a mating second portion, the surface 104 is in the interior of the disc nucleus replacement. The first portion 100 also includes a generally semi-circular outer surface 106, a preferably flat top surface 108, and a preferably flat bottom surface 110. A dovetail socket 112 is formed into the surface 104 into the body of the first portion 100, extending across the entire surface 104. The socket 112 includes is defined by a bottom surface 114, a top surface 116, and a rear surface 118, and is advantageously trapezoidal in shape, as are dovetail sockets, so that when a mating tail of a sliding dovetail joint is slid into the socket, the tail is captured in the socket.

The outer surface 106 includes a convex curved portion 130 adjacent to the socket 112 which extends to a generally flat, angled face 132, which in turn extends towards the plane 102 and a concave curved surface 134. A throughbore 140 is formed through the first portion 100 from the face 132, and is preferably angled toward the plane 102. The bore 140 is sized to receive a screw (not illustrated) which, when inserted through the bore, extends into a mating second portion (described elsewhere herein) and secures the first and second portions together. The bore 140 is preferably countersunk 142. Because of the dovetail joint, it is not necessary for the first portion to be used with two screws to secure the two portions together, despite the planar symmetry of the first portion, although two screws can be used.

Figure 4:
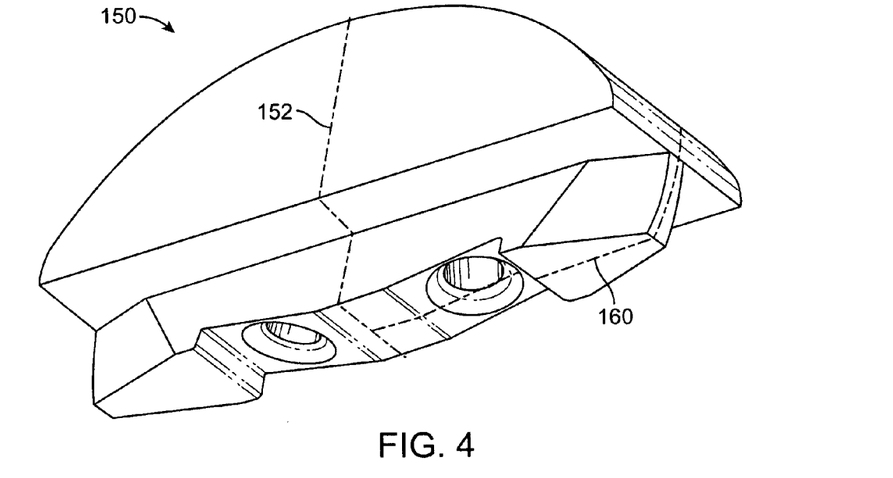
FIG. 4 illustrates a perspective view of a second embodiment of a second half of a two-piece disc replacement embodying principles of the present invention.
Figure 5:
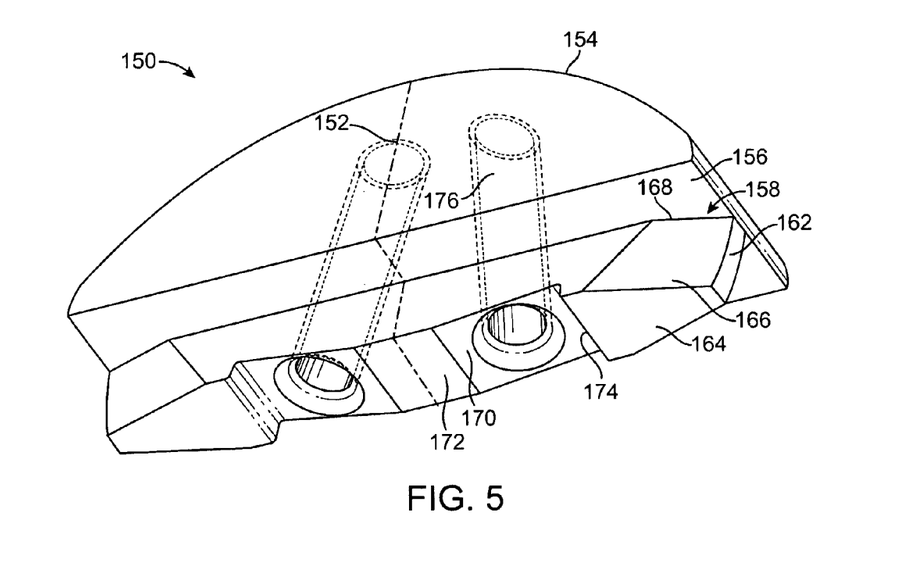
FIG. 5 illustrates a wire-frame perspective view of the second half illustrated in FIG. 4.

FIGS. 4 and 5 illustrate a second embodiment of a second portion 150 which is configured to mate with the first portion 100. As with other embodiments described herein, the second portion 150 is advantageously, yet not necessarily, planar-symmetrical about planes 152, 160. The second portion 150 includes a generally semi-circular outer surface 154 and a generally flat interior surface 156. A tail 158 (of a dovetail joint) extends laterally from the surface 156, and is preferably bisected by the plane 160. The tail 158 includes an endface 162 oriented outwardly, an interior surface 164, slanted upper surfaces 166, 180, a generally flat surface 170, and a shoulder 174 between the surfaces 164 and 170, and a generally flat surface 172 which is bisected by the plane 152. These surfaces, and their complementary surfaces on the other sides of the planes, define the outer surface of the tail 158 so that cross-sections of the tail parallel to the plane 152 are advantageously, yet not necessarily, trapezoidal, e.g., with the surface 166 slanted towards the plane 160 towards the joint 168 where the tail 158 meets the surface 156. The second portion 150 also includes a blind bore 176 extending from a countersunk end at the surface 170 towards the surface 154, preferably angled towards the plane 152. The bore 176 is configured to align with the bore 140 of the first portion 100, so that when a screw is advanced through the bore 140, it can easily enter the bore 176 and secure the two portions together. For this purpose, the bore 176 can have a reduced inner diameter relative to the bore 140, for use with self-tapping screws, or can include threads on the inner surface of the bore for mating with correspondingly configured external threads on such a screw.

Figure 6:
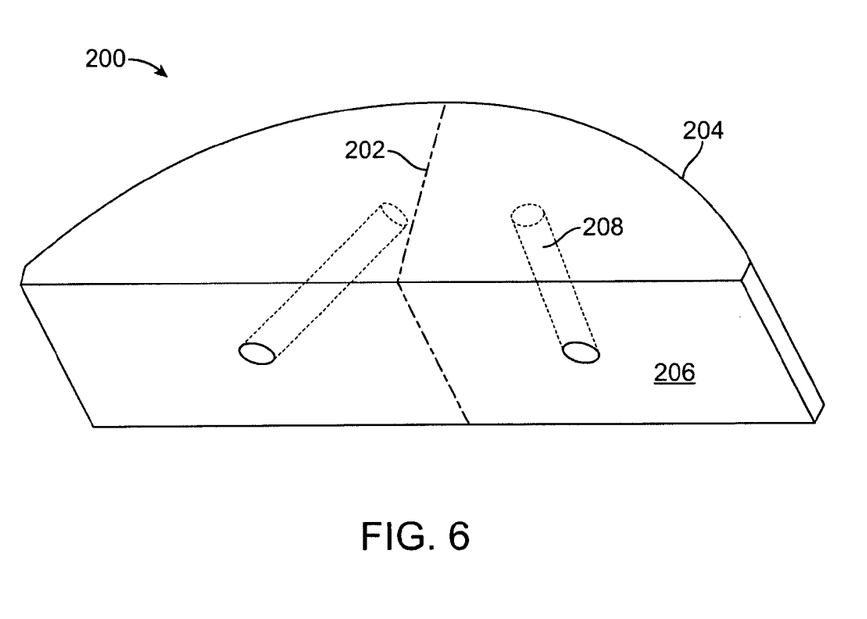
FIG. 6 illustrates a wire-frame perspective view of a first embodiment of a second half of a two-piece disc replacement embodying principles of the present invention.

FIG. 6 illustrates a first embodiment of a second portion 200 of a disc nucleus replacement embodying principles of the present invention, and is configured to mate with the first portion 10. The second portion 200 is symmetrical about and bisected by a vertical plane 202, and includes a generally semi-circular outer surface 204, a generally flat surface 206 configured to abut a surface of the first portion 10 (described below), and a blind bore 208, also preferably angled towards the plane 202, having an inner diameter smaller than a corresponding bore in the first portion 10, or having internal threads.

Figure 7:
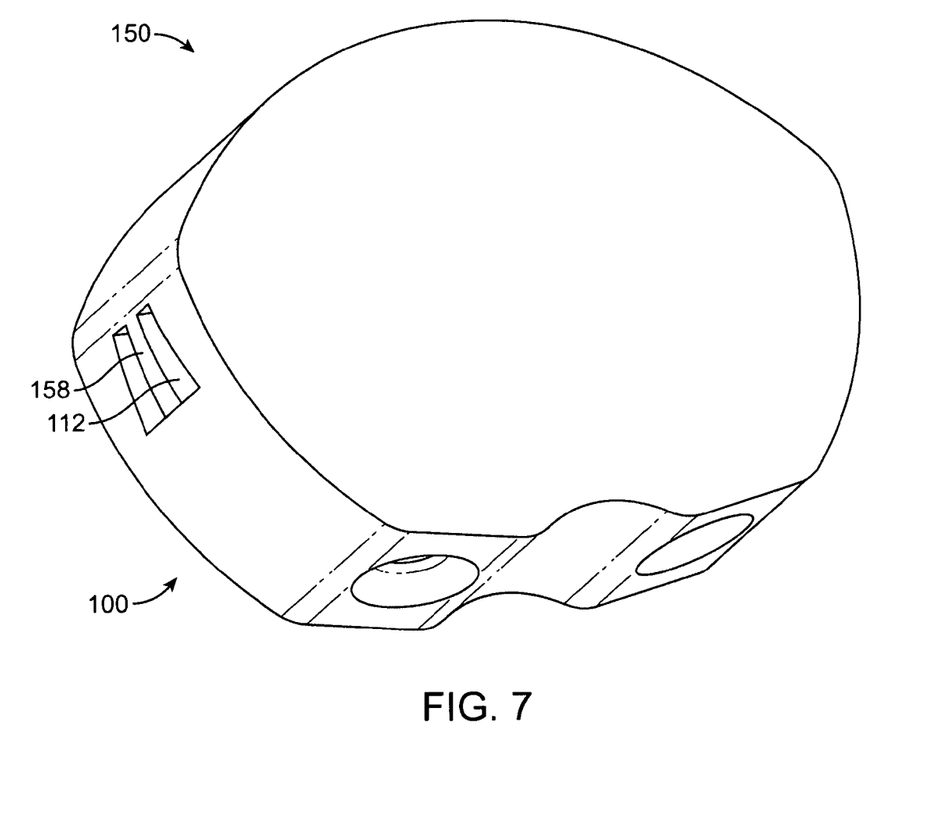
FIG. 7 illustrates a perspective view of the second embodiment, including the first and second halves assembled together.
Figure 8:
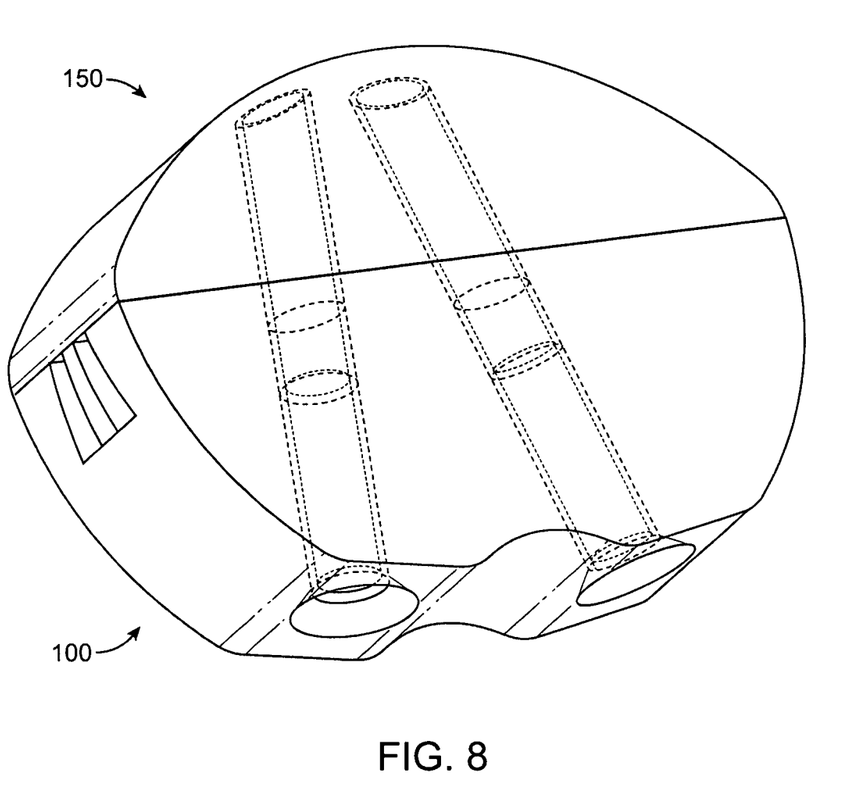
FIG. 8 illustrates a wire-frame perspective view of the assembly illustrated in FIG. 7.
Figure 9:
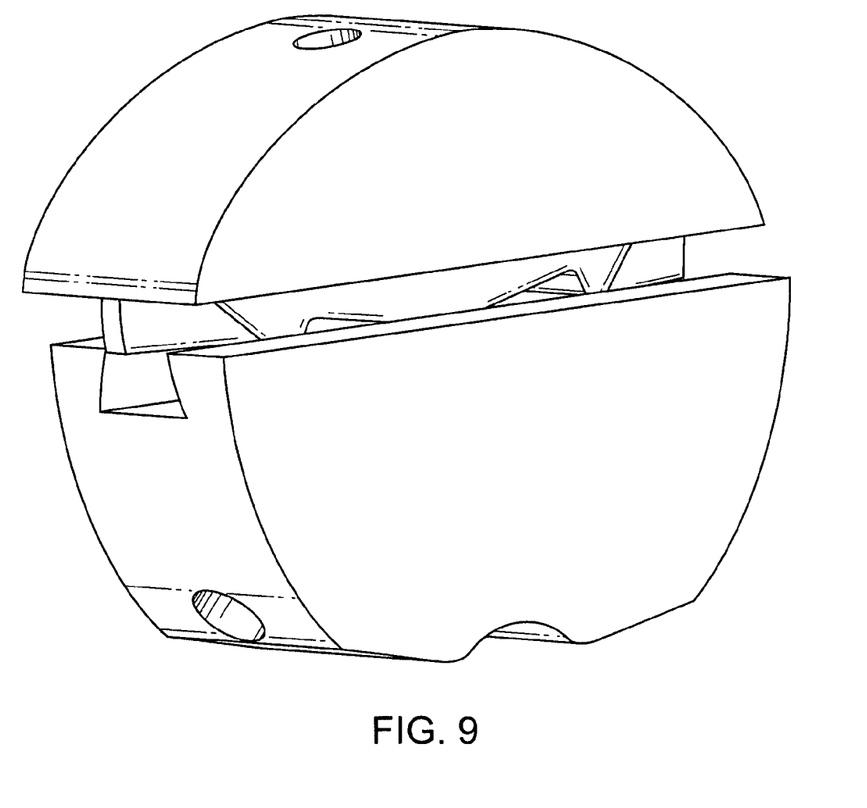
FIG. 9 illustrates a perspective view of the second embodiment, including the first and second halves, in the process of being assembled together.

FIGS. 7 and 8 illustrate the first and second portions 100, 150, of the second embodiment, assembled together to form a disc nucleus replacement, and showing the end of the dovetail joint formed by the socket 112 and the tail 158. FIG. 9 illustrates another view of the first and second portions 100, 150.

Figure 10:
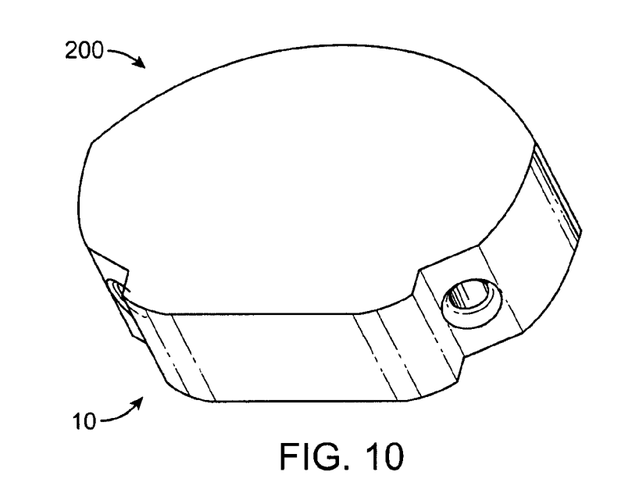
FIG. 10 illustrates a perspective view of the first embodiment, including the first and second halves assembled together.
Figure 11:
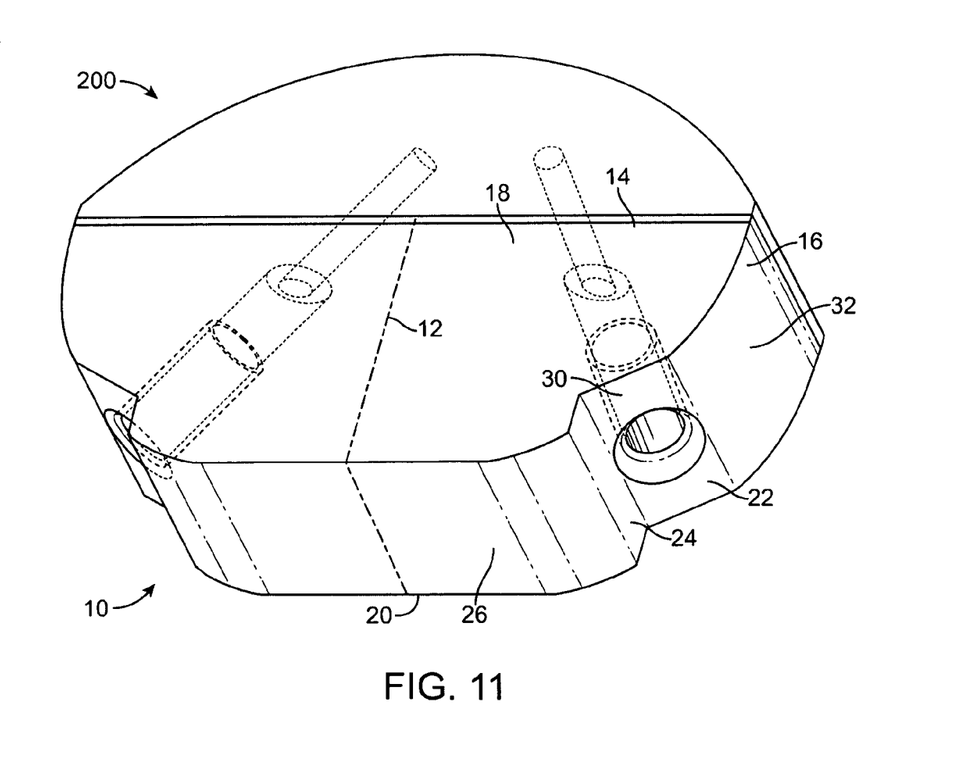
FIG. 11 illustrates a wire-frame perspective view of the assembly illustrated in FIG. 10.

FIGS. 10 and 11 illustrate the first embodiment of the first portion 10 assembled together with the first embodiment of the second portion 200, forming a disc nucleus replacement embodying principles of the present invention. The first portion 10 includes a generally flat interior surface 14, a generally semi-circular outer surface 16, a generally flat upper surface 18, and generally flat lower surface 20. The outer surface 16 includes a convex curved surface 32 and a generally flat, angled surface 22, the surface 32 extending between the flat interior surface 14 and the surface 22. The surface 16 further includes a laterally protruding extension 26 which forms a shoulder 24 with the surface 22. A throughbore 30, preferably countersunk, extends from the surface 22 through the body of the first portion 10, is preferably angled toward the plane 12, and is oriented and positioned to line up with the bore 208 in the second portion 200. In this manner, when the two portions 10, 200 are implanted in situ, the bores 30, 208 align and a screw can be advanced through the bore 30 and into the bore 208 to secure the two portions 10, 200 together.

Exemplary methods embodying principles of the present invention will now be described with reference to the drawing figures. A patient in need of a disc nucleus replacement is prepped, access is made to the damaged or diseased disc, and the core or nucleus of the patient's disc is removed. Advantageously, these procedures are performed via two lateral incisions in the disc. Once the diseased nucleus has been removed, the surgeon pushes one portion of a two-piece disc nucleus replacement through one of the lateral incisions and into place in the center of the patient's disc. The surgeon then pushes the mating portion of the two-piece disc nucleus replacement through the same or the other lateral incision, into the space previously occupied by the disc's natural nucleus, and adjacent to and into alignment with the first portion of the two-piece disc nucleus replacement. If the two-piece disc nucleus replacement includes a dovetail joint as described herein, when inserting the second portion (which may be a portion of the two-piece disc nucleus replacement with either a tail or a socket), the surgeon aligns the two parts of the dovetail joint so that pushing the portion into place also includes mating together the two portions of the two-piece disc nucleus replacement. The surgeon then may position one or two screws in the bores of the assembled two-piece disc nucleus replacement, and further secure the two portions together.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A disc nucleus replacement comprising:
   a first portion having a top, a bottom, a generally semi-circular lateral outer surface extending between the top and the bottom, a flat outer lateral surface extending between the top and the bottom, and at least one bore extending through the first portion from the semi-circular lateral outer surface to the flat outer surface;
   a second portion having a top, a bottom, a generally semi-circular lateral outer surface extending between the top and the bottom, a flat outer lateral surface extending between the top and the bottom, and at least one bore extending through the second portion from the flat outer surface towards the semi-circular lateral outer surface;
   wherein the at least one bore of the first portion, the at least one bore of the second portion, the semi-circular lateral outer surface of the first portion, and the semi-circular lateral outer surface of the second portion are mutually configured and arranged so that when the first and second portions are oriented with the flat surfaces abutting and the semi-circular lateral outer surfaces forming a generally circular form, the at least one bore of the first portion aligns with the at least one bore of the second portion to permit a single screw to be positioned therein;
wherein the at least one bore of the first portion comprises two bores, and the at least one bore of the second portion comprises two bores; and
wherein said generally semi-circular lateral outer surface of the first portion includes a lateral extension between said two bores.

2. The disc nucleus replacement according to claim 1, wherein the first portion and the second portion are both formed of a biocompatible material.

3. The disc nucleus replacement according to claim 2, wherein said biocompatible material is selected from the group consisting of titanium, peek, and a ceramic.

4. The disc nucleus replacement according to claim 1, wherein said first portion is symmetrical about a vertical plane extending through the top and bottom surfaces and through the geometric center of the first portion.

5. The disc nucleus replacement according to claim 4, wherein said second portion is symmetrical about a vertical plane extending through the top and bottom surfaces and through the geometric center of the second portion.

6. The disc nucleus replacement according to claim 1, wherein said first portion is symmetrical about a horizontal plane extending through the lateral surfaces and through the geometric center of the first portion.

7. The disc nucleus replacement according to claim 6, wherein said second portion is symmetrical about a horizontal plane extending through the lateral surfaces and through the geometric center of the second portion.

8. A disc nucleus replacement comprising:
a first portion having a top, a bottom, a generally semi-circular lateral outer surface extending between the top and the bottom, a flat outer lateral surface extending between the top and the bottom, and two bores extending through the first portion from the semi-circular lateral outer surface to the flat outer surface;
a second portion having a top, a bottom, a generally semi-circular lateral outer surface extending between the top and the bottom, a flat outer lateral surface extending between the top and the bottom, and two bores extending through the second portion from the flat outer surface towards the semi-circular lateral outer surface;
wherein the two bores of the first portion, the two bores of the second portion, the semi-circular lateral outer surface of the first portion, and the semi-circular lateral outer surface of the second portion are mutually configured and arranged so that when the first and second portions are oriented with the flat surfaces abutting and the semi-circular lateral outer surfaces forming a generally circular form, the two bores of the first portion align with the two bores of the second portion to permit a two screws to be positioned therein; and
wherein the generally semi-circular lateral outer surface of the first portion comprises two laterally offset recesses extending between the top and bottom, each of the two bores in the first portion originating in one of said two recesses.

* * * * *